United States Patent [19]

Sullivan et al.

[11] 4,178,241

[45] Dec. 11, 1979

[54] METHOD OF REMOVING UREA AND/OR CREATININE

[76] Inventors: Thomas E. Sullivan, 9401 Persimmon Tree Rd., Potomac, Md. 20845; Oscar L. Wright, 11 Kathy La., Monroe, La. 71203

[21] Appl. No.: 944,130

[22] Filed: Sep. 20, 1978

[51] Int. Cl.$^2$ ............................................. B01D 15/04
[52] U.S. Cl. ........................................ 210/24; 210/40; 260/555 R; 260/555 C; 548/308
[58] Field of Search ................... 548/308; 260/555 R, 260/555 C; 210/24, 40

[56] References Cited

U.S. PATENT DOCUMENTS

| | | | |
|---|---|---|---|
| 2,577,202 | 12/1951 | Lien et al. | 260/555 R |
| 2,588,602 | 3/1952 | Adams et al. | 260/555 R |
| 2,705,727 | 4/1955 | Graham | 260/555 R |
| 4,012,317 | 3/1977 | Kuntz et al. | 210/24 |

FOREIGN PATENT DOCUMENTS 470838  1/1951  Canada .................................. 260/555R

OTHER PUBLICATIONS

Swern Industrial and Engineering Chemistry 1955, vol. 47, pp. 216–221.

*Primary Examiner*—Natalie Trousof

[57] ABSTRACT

The present invention pertains to a method for removing urea and creatinine from aqueous solutions by contacting such solutions with a polymer selected from the group consisting of: p-mercapto polystyrene; p-mercaptoacetic polystyrene; dinitro-p-mercaptoacetic polystyrene; p-nitropolystyrene; and p-amino polystyrene.

1 Claim, No Drawings

METHOD OF REMOVING UREA AND/OR CREATININE

RELATED APPLICATION

This application is related to Applicants' copending application Ser. No. 789,498, filed Apr. 22, 1977.

BACKGROUND OF THE INVENTION

In the human metabolism of proteins, the principle waste products are urea and creatinine. The normal daily production of urea is 30 grams and 1.5 grams of creatinine. In the healthy human, these materials are removed from the blood stream by the kidneys and excreted from the body in the urine. In the case of a diseased or damaged kidney that is unable to perform its normal function, current medical practice provides for the removal of urea and creatinine by means of the extracorporeal treatment of the patient's blood in a renal dialysis device employing specially designed semipermeable membranes. The blood circulates in contact with one face of a membrane, the other face of which is in contact with an aqueous solution of chemical composition similar to that of blood. In this aqueous "dialysis bath" the concentration of urea and creatinine must be kept as low as possible in order for the urea and creatinine in the blood to continue to flow across the membrane as a result of a high concentration gradient. This requires either the replacing of the dialysis bath by a new bath when the gradient decreases, or the treatment of the dialysis bath in order to either completely or partially remove the urea and creatinine. One method used for lowering the waste product concentration in the used bath consists of introducing it into a storage reservoir of fresh solution before it is reused, but this soon leads to the use of large volumes of dialysis liquid which must in any case ultimately be discarded. A number of attempts have been made to remove urea and creatinine by treating the used dialysis bath with ion exchange resins or activated charcoal, and a method has been cited (U.S. Pat. No. 4,012,317, Mar. 15, 1977, Kuntz et al) that uses a polymer for removing urea. However, the efficiency of all previously tried compounds, especially in the case of urea, has proved to be quite low.

The present invention pertains to a method for removing urea and creatinine from aqueous solutions by contacting such solutions with a polymer selected from the group consisting of:

1. p-Mercapto polystyrene
2. p-Mercaptoacetic polystyrene
3. Dinitro-p-mercaptoacetic polystyrene
4. p-Nitropolystyrene
5. p-Amino polystyrene The above polymers were prepared as follows:

1. Preparation of p-mercaptopolystyrene: This compound was produced by the reduction of polystyrene sulfonic acid. 190 gms (approximately 50% water) of polystyrene sulfonic acid were stirred with 300 mls of 10% sulfonic acid while 110 gms of powdered zinc was added, 2-3 gms at a time, over a period of 2 hrs. The reaction was vigorous at first, but slowed as sulfuric acid was used up. Small amounts of conc. sulfuric acid were added from time to time, to maintain the activity of the zinc reaction. When all the zinc had been added, the reaction mixture was stirred overnight. The product was filtered and washed with water. Since small amounts of zinc dust were occasionally found in the residue, a small amount of dilute hydrochloric acid was used as a final wash. This functional polymer reacts readily with nitric acid.

2. Preparation of p-mercaptoacetic polystyrene. 100 gms of the functional polymer p-mercapto polystyrene described and prepared as above, was stirred with 500 mls of water which contained 25 gms of sodium hydroxide, for a 12 hr. period. Then 40 gms of the sodium salt of chloracetic acid were slowly added. The reaction was vigorous at first but slowed as the additions were made. When the additions were complete, the mixture was stirred for an additional 2 hrs. The product was filtered and washed twice with water, once with dilute chloracetic acid and then twice more with water.

3. Preparation of dinitro-p-mercaptoacetic polystyrene. The product p-mercaptoacetic polystyrene was not futher purified, but instead was added bit by bit, with stirring, to a solution of 50 mls of concentrated nitric acid and 50 mls of sulfuric acid. The first additions reacted violently; and although the reaction was cooled in an ice bath, only small increments could be added at a given time. The reaction mixture was stirred for an additional 30 minutes after all the resin had been added. The product was filtered, washed with 10% sodium bicarbonate solution and the unreacted bicarbonate was removed by repeated washings with water.

4. Preparation of p-nitropolystyrene. 10.7 gms of polystyrene was slurried in 50 mls of concentrated sulfuric acid and stirred, as a mixture of 50 mls concentrated nitric acid and 50 mls concentrated sulfuric acid was added. The reaction was exothermic and rapid at first but slowed when about 50% of the acid had been added. The product was filtered, washed with water, and dried in air.

5. Preparation of p-amino polystyrene. p-nitropolystyrene prepared as described above was slurried with approximately 350 mls of 10% sulfuric acid solution. 125 gms of zinc dust were slowly added. There was an obvious reaction, but the color change was only slight. The reaction mixture was stirred overnight, after which it was filtered and washed with dilute sulfuric acid and water, and finally with very dilute sodium bicarbonate and water.

The functional polymers decribed above were prepared specifically for removal of urea and creatinine from biological solutions. Ideally each 200 gms of functional polymer should remove 30 gms of urea and 1.5 gms of creatinine (These correspond to the normal daily adult productions). Preliminary testing of each functional polymer was against separate aqueous solutions of urea (75 gms/L) and creatinine (3.75 gms/L). The testing was performed in the following manner: Five gms of the functional polymer were contacted with 10 mls of urea or creatinine solution in a 25 ml Erlenmeyer flask. The flasks were sealed and shaken in a 37° C. water bath for a period of 12 hrs. Urea and creatinine concentrations were determined before and after contact with each functional polymer to determine the amount of each removed by polymer chemisorption. These results are shown in Table 1. Urea and creatinine uptake by 200 gms of functional polymer was calculated from the results of these batch experiments. Also shown in the table are the calculated percent removal of daily production of the nitrogenous compounds.

TABLE

Testing of Functional Polymers against Urea (75 gms/L) Solutions and creatinine (3.75 gms/L) Solutions

| | Urea adsorbed (mg) per gm of polymer | Calculated urea adsorbed (gms) per 200 gms polymer | % of normal adult production of urea adsorbed | Creatinine (mg) adsorbed per gm of polymer | Calculated creatinine (gms) adsorbed per 200 gms p. | % of normal adult daily production of creatinine ads |
|---|---|---|---|---|---|---|
| p-mercapto polystyrene | | | | | | |
| Batch A | 96 | 19.2 | 64 | 6.9 | 1.4 | 93.3 |
| Batch B | 43 | 8.6 | 29 | 7.1 | 1.4 | 93.3 |
| p-mercapto acetic polystyrene | | | | | | |
| Batch A | 74 | 14.8 | 49 | 7.0 | 1.4 | 93.3 |
| Batch B | 58.4 | 11.7 | 39 | 7.2 | 1.4 | 93.3 |
| Batch C | 70 | 14.0 | 47 | 7.1 | 1.4 | 93.3 |
| Dinitro-p-mercapto acetic polystyrene | 60.3 | 12.1 | 40 | 7.1 | 1.4 | 93.3 |
| p-nitropolystyrene | 7.5 | 1.5 | 5 | * | — | — |
| p-amino polystyrene | 12 | 2.4 | 8 | * | — | — |

*Experiments not performed in view of poor urea chemisorption

We also contemplate that the five polymers set forth above can be used for the modification of blood, other biological fluids, or tissues whereby specific desirable substances can be either extracted from or added to the blood, biological fluid, or tissue.

We contemplate that the polymers of the present invention are useful for the same purposes and can be used in the same manner as the blood compatible polymers set forth in our copending application Ser. No. 789,498 filed Apr. 21, 1977, the disclosure of which is incorporated herein by reference.

We claim:

1. The method of removing urea and/or creatinine of biological origin from aqueous solutions containing the same, which method comprises contacting such aqueous solutions with a polymer selected from the group consisting of
   (a) p-Mercapto polystyrene
   (b) p-Mercaptoacetic polystyrene
   (c) Dinitro-p-mercaptoacetic polystyrene
   (d) p-Nitro polystyrene, and
   (e) p-Amino polystyrene,
said polymer adsorbing at least some of the urea and/or creatinine from the aqueous solution.

* * * * *